United States Patent [19]
Gondo

[11] Patent Number: 5,349,960
[45] Date of Patent: Sep. 27, 1994

[54] ULTRASONIC DIAGNOSIS APPARATUS

[75] Inventor: Masahiko Gondo, Fuchu, Japan

[73] Assignee: Olympus Optical Co., Ltd., Tokyo, Japan

[21] Appl. No.: 953,811

[22] Filed: Sep. 30, 1992

[30] Foreign Application Priority Data

Oct. 1, 1991 [JP] Japan ............................. 3-253679
Oct. 24, 1991 [JP] Japan ............................. 3-277805

[51] Int. Cl.$^5$ ................................................ A61B 8/06
[52] U.S. Cl. ................................................ 128/661.09
[58] Field of Search ......... 128/660.03, 661.09–661.10; 73/861.25

[56] References Cited

U.S. PATENT DOCUMENTS

| | | | |
|---|---|---|---|
| 4,217,909 | 8/1980 | Papadofrangakis et al. | 128/661.01 X |
| 4,325,257 | 4/1982 | Kino et al. | 73/626 |
| 4,799,490 | 1/1989 | Namekawa | 128/661.09 |
| 4,917,097 | 4/1990 | Proudian et al. | 128/662.06 |
| 5,148,808 | 9/1992 | Satake | 128/661.09 X |
| 5,168,877 | 12/1992 | Yamaguchi et al. | 128/661.09 |
| 5,230,340 | 7/1993 | Rhyne | 128/661.01 |

FOREIGN PATENT DOCUMENTS

| | | |
|---|---|---|
| 0008517 | 3/1980 | European Pat. Off. . |
| 0189180 | 7/1986 | European Pat. Off. . |
| 0359130 | 3/1990 | European Pat. Off. . |

OTHER PUBLICATIONS

C. Kasai, et al, "Real–Time Two–Dimensional Blood Flow Imaging Using Ultrasound Doppler", Japanese Journal of Applied Physics/Supplement 26–1, vol. 26, 1987, pp. 9–13.

Primary Examiner—Francis Jaworski
Attorney, Agent, or Firm—Stevens, Davis, Miller & Mosher

[57] ABSTRACT

A plurality of vibrating elements are provided to form an array and successive vibrating elements are selected to emit ultrasonic pulses toward a cavity of a living body. Ultrasonic waves reflected by tissues and blood cells in the blood vessel are received by the vibrating elements and are converted into echo signals. The echo signals are supplied to an orthogonal detector together with a reference signal and are converted into real and imaginary parts of complex signals which are stored in memories as the wave surface data. The wave surface data is read out at suitable timings to obtain an ultrasonic reflection image data such that a focus point is formed in a given space. By processing the reflection image data by a spectrum distribution detector, a spatial frequency is derived. A reflection strength is derived from a DC component of the spatial frequency and a B-mode ultrasonic image is displayed. From an AC component of the spatial frequency a velocity and a direction of a blood stream are derived and are displayed in superimposition with the B-mode ultrasonic image. In this manner, it is possible to detect accurately a blood stream having a very low velocity. Also a blood stream flowing in a direction parallel with a direction in which the vibrating elements are arranged can be measured.

6 Claims, 10 Drawing Sheets

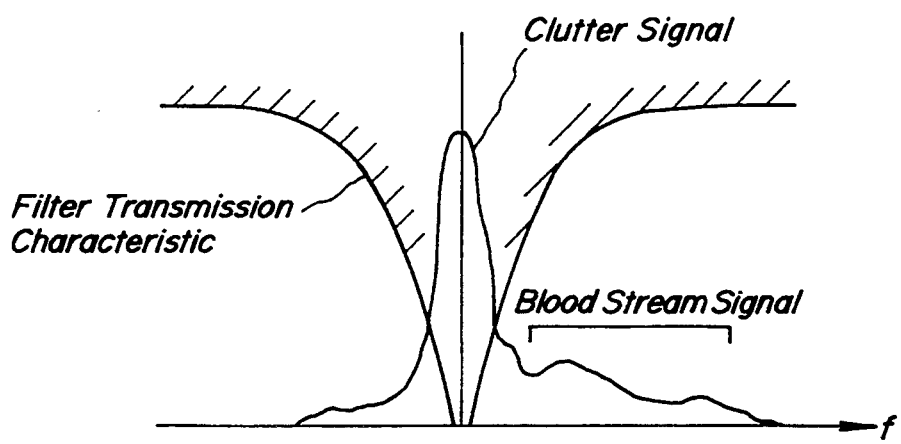
FIG_2
PRIOR ART

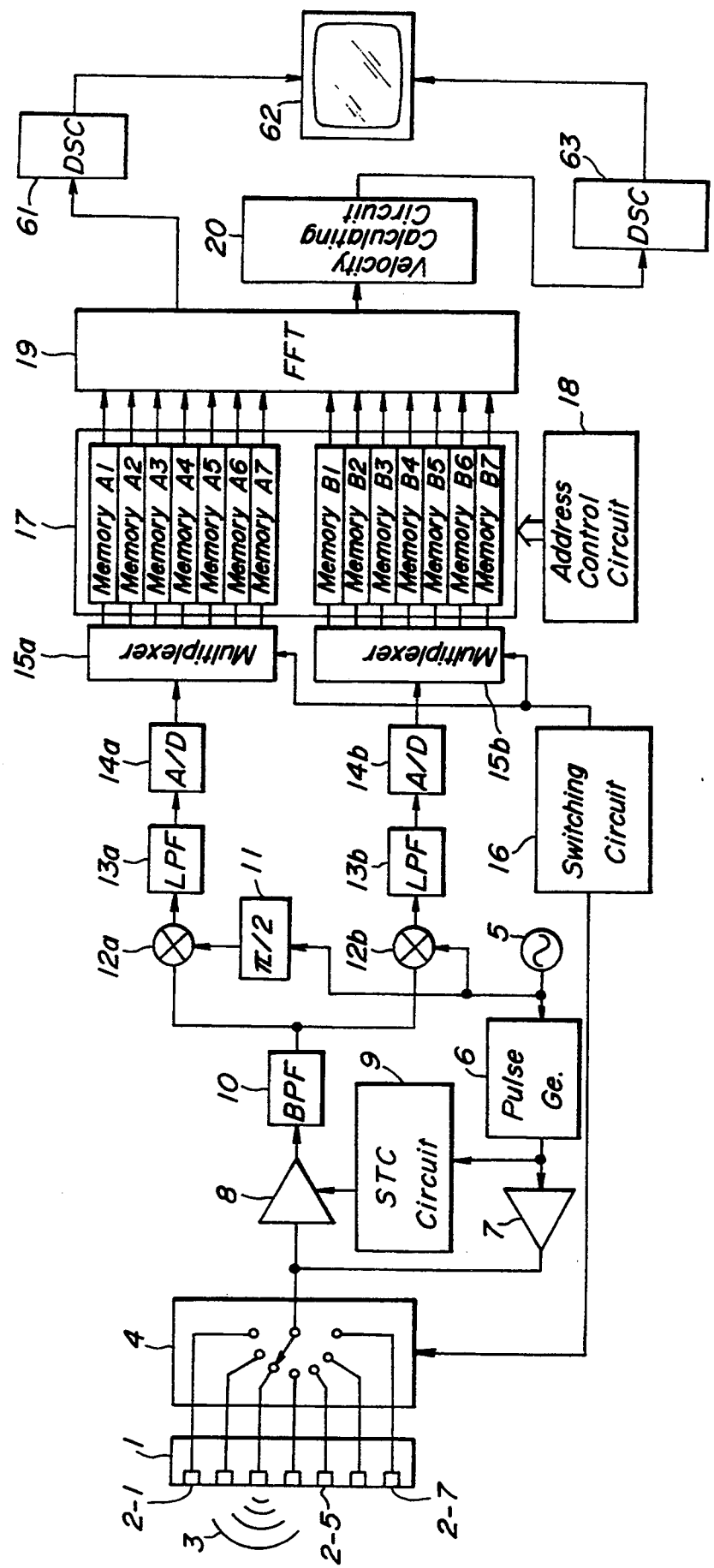

FIG_4
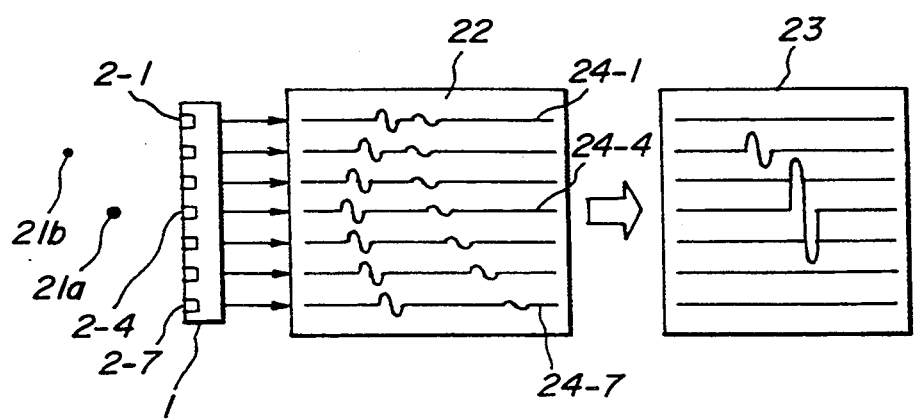

FIG._5A
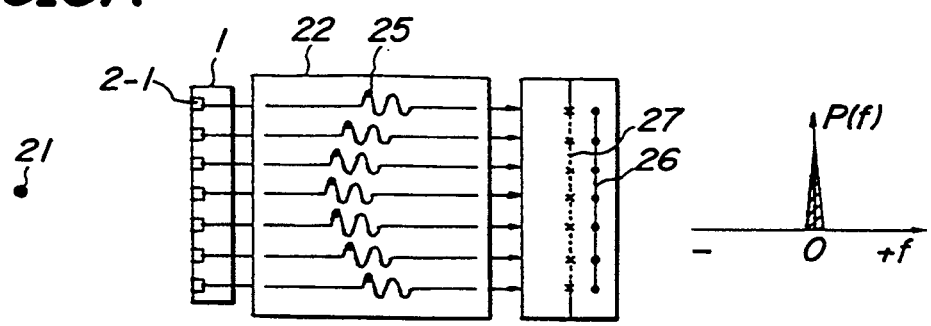
FIG._5B
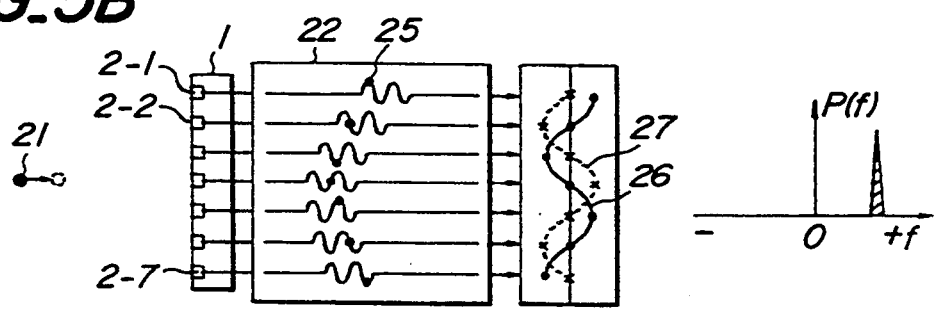
FIG._5C
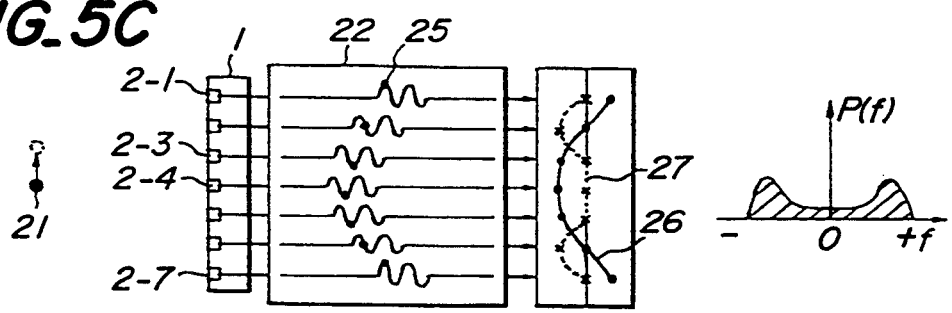

FIG_6
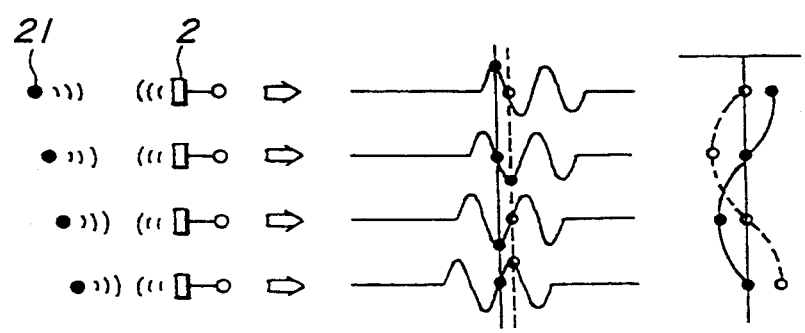

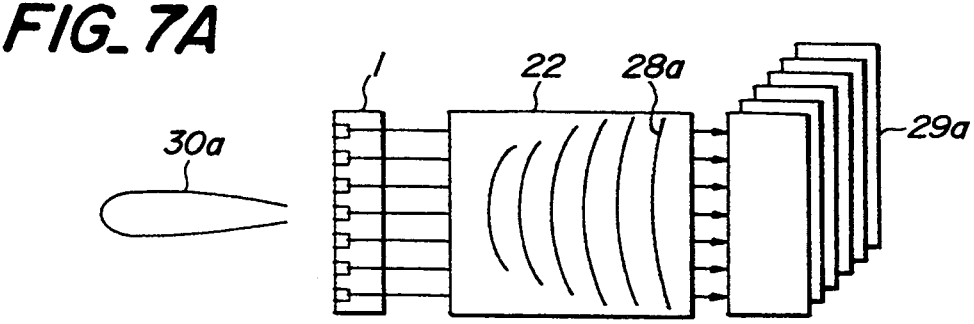
FIG._7A
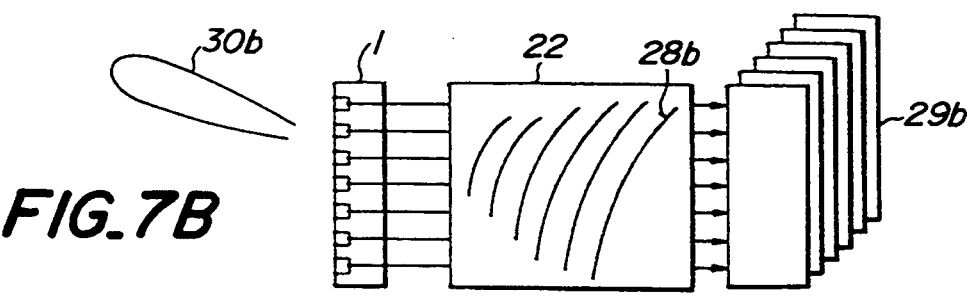
FIG._7B
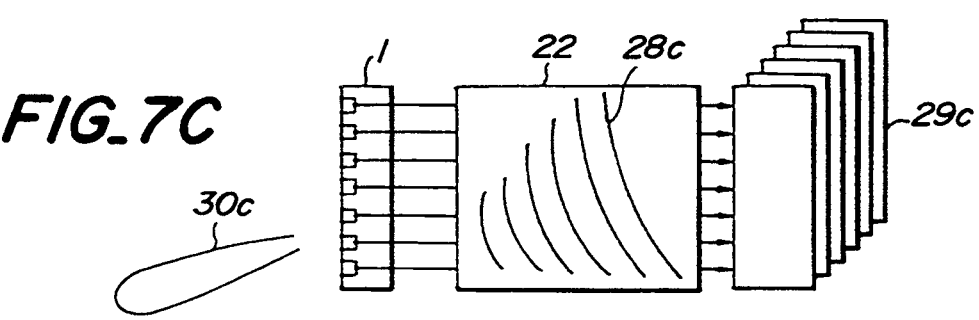
FIG._7C

FIG_8
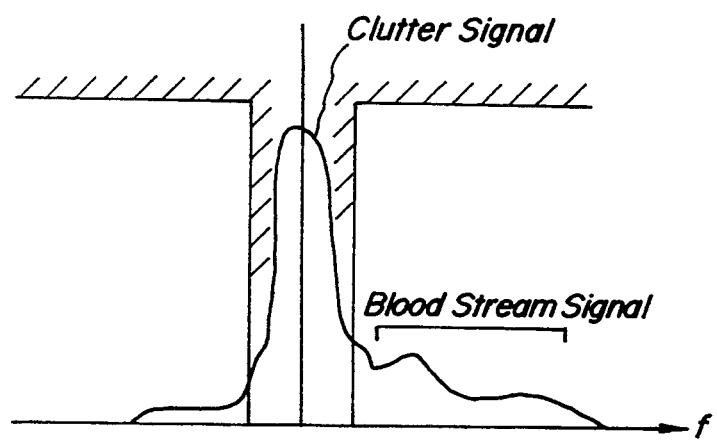

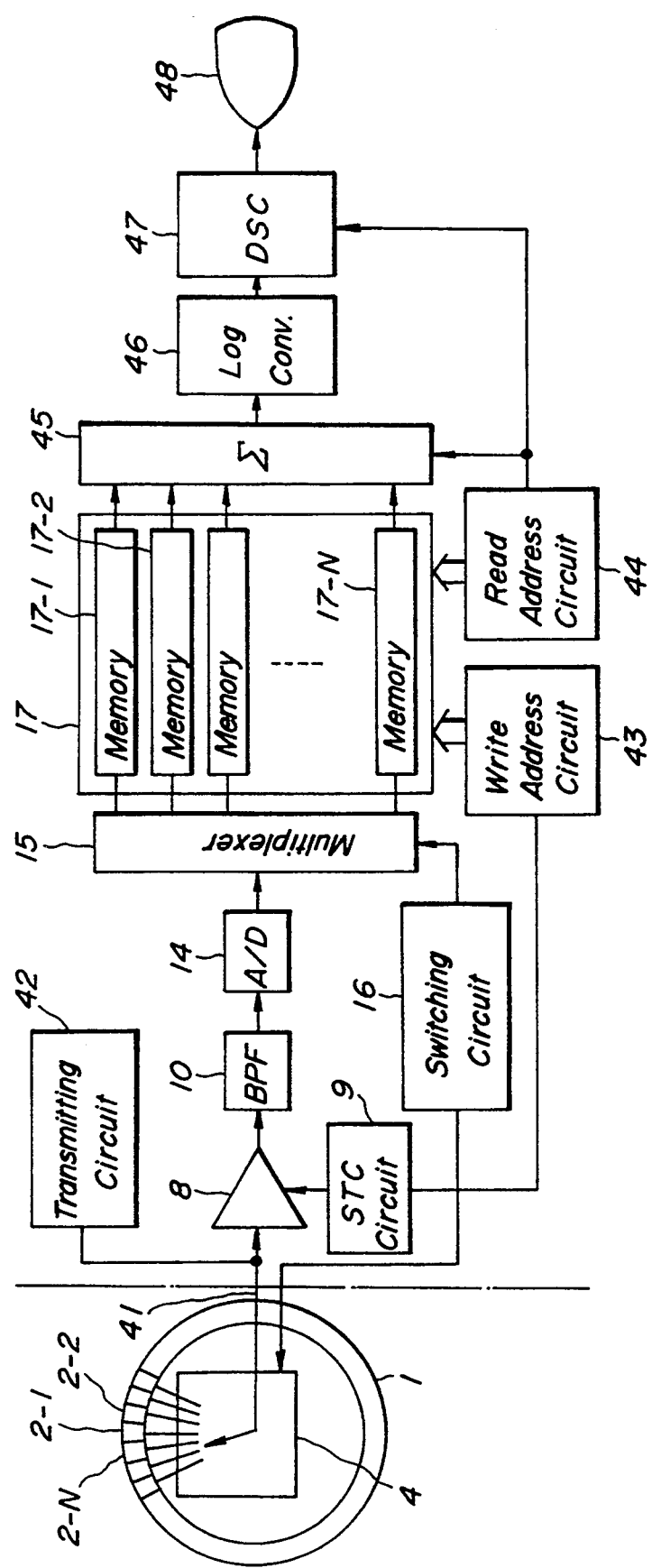

FIG_10A  FIG_10C
FIG_10B
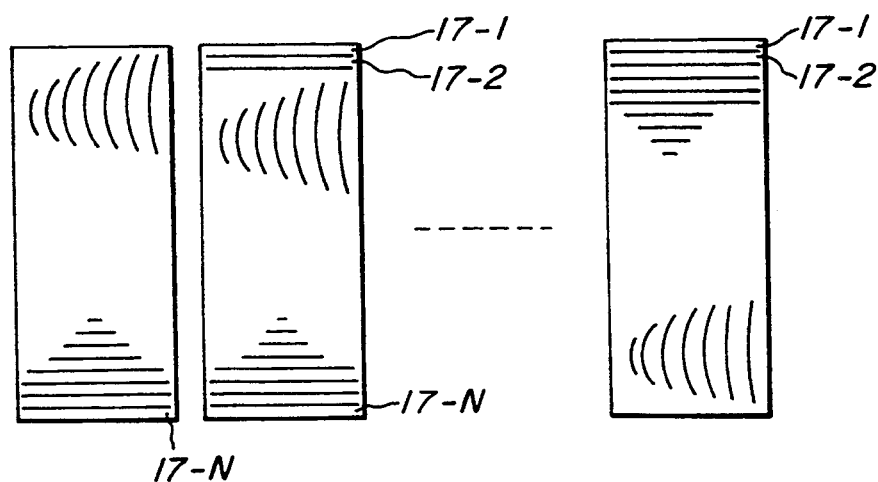
FIG_11
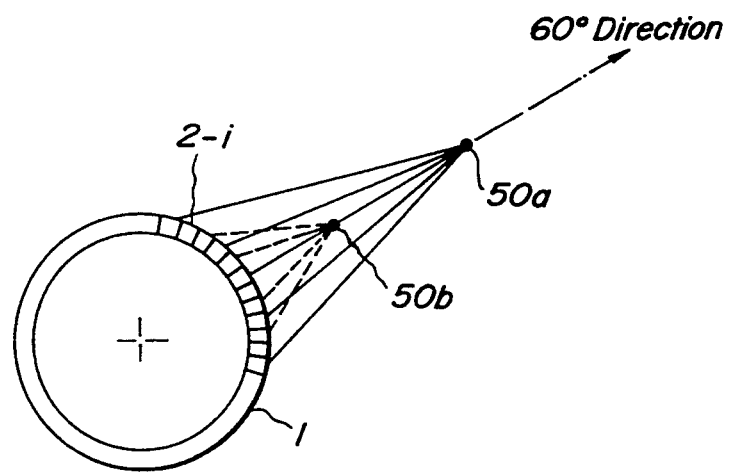

ULTRASONIC DIAGNOSIS APPARATUS

BACKGROUND OF THE INVENTION

FIELD OF THE INVENTION

The present invention relates to an ultrasonic diagnosing apparatus for measuring a moving velocity of a moving object, such as a blood in a living body, and more particularly to an ultrasonic diagnosing apparatus for displaying a blood stream in superimposition on an ultrasonic image.

An ultrasonic diagnosing apparatus for detecting a distribution of a blood stream by utilizing the Doppler effect and displaying the blood stream in superimposition on an ultrasonic image has been known as a color Doppler apparatus and has been widely used. In principle, in such a color Doppler apparatus a pulsatory ultrasonic beam is emitted from an ultrasonic vibrating element array with a constant time interval. A time period from an instant at which the ultrasonic beam is emitted toward an object to a timing at which an ultrasonic wave reflected by the object is received by the vibrating element array to produce an echo signal is measured and a variation in frequency of a received signal is measured to detect a position and a movement of the object. Initially the color Doppler apparatus was utilized to diagnose the circulatory system of the human being such as the heart, but recently it has been used to diagnose other organs such as the stomach due to the fact that the color Doppler apparatus can provide a large amount of information.

FIG. 1 is a block diagram illustrating the known color Doppler apparatus. A reference numeral 101 denotes a vibrating element array, 102 denotes vibrating elements, 103 delay circuits, 104 denotes a switching circuit, 105 denotes a signal generator, 106 denotes a pulse generator, 107 summing denotes a circuit, 108 denotes receiving amplifier, 109 band pass filter (BPF), 110 denotes 90-degree phase shifter, 111a, 111b denote multiplying circuits, 112a, 112b denote low pass filters (LPF), 113a, 113b denote A/D converters, 114 denote a MTI filter for extracting a blood stream component, and a reference numeral 115 represents an autocorrelation circuit for detecting a frequency component.

An output signal of the signal generator 105 is supplied to the pulse generator 106 to produce a pulse having a center frequency $f_0$. The pulse is then supplied to the vibrating element array 101 by means of the switching circuit 104 and delay circuit 103. By suitably operating the switching circuit 104, respective vibrating elements 102 of the array 101 are energized such that an ultrasonic beam 116 is emitted in a given direction. The ultrasonic beam 116 is reflected by red blood cells contained in blood flowing through a blood vessel 117 and is received by the vibrating elements 102 and is converted into echo signals. The echo signals are supplied to the summing circuit 107 by means of the delay circuits 103 and switching circuit 104 and are summed up thereby. An output signal of the summing circuit 107 is amplified by the receiving amplifier 108 to a suitable level and then is supplied to BPF 109 to cut off noise other than a desired frequency component. Then, the output signal of BPF 109 is supplied to an orthogonal detector, constituted by the multiplying circuits 111a and 111b and 90-degree phase shifter 110, to detect a difference frequency component $\Delta f$ between the orthogonally detected output signal and the reference signal generated by the signal generator 105.

The difference frequency $\Delta f$ represents the Doppler frequency of the blood stream in the blood vessel 117 and is dependent upon an angle between the ultrasonic beam 116 and the blood vessel 117. That is to say, the Doppler frequency represents a component Vd of the blood stream velocity V in the direction of the ultrasonic beam. In this manner, the Doppler frequency depends largely upon the angle between the ultrasonic beam 116 and the blood vessel 117 under inspection.

The output signals from the multiplying circuits 111a, 111b are supplied, via LPFs 112a, 112b, to A/D converters 113a, 113b and are converted into digital signals. Then, the digital signals are supplied to the MTI filter 114 and a DC component (clutter component), which corresponding to echo signal components reflected from stationary tissues, is removed to extract a signal component representing an echo signal component reflected from the blood stream. The thus derived blood stream component is supplied to the autocorrelation circuit 115 to detect the above mentioned difference frequency component $\Delta f$. This component is then displayed on a display monitor by means of a digital scan converter. The display monitor displays a B-mode ultrasonic image representing the strength of the ultrasonic wave reflected by the stationary tissues in the living body in superimposition therewith. The blood stream signal is displayed with a special color such as red and blue in contrast with the B-mode ultrasonic image. In the known color Doppler apparatus, the Doppler component fluctuates greatly, and thus the ultrasonic beam is emitted in the same direction about ten times and an average of the detected blood stream components is derived in order to attain a necessary measuring accuracy.

In the known color Doppler apparatus explained above, it is difficult to separate the blood stream signal from the clutter component reflected from the stationary objects when the blood stream flows at a relatively low velocity, so that the measurement could not be carried out practically. The separation between the Doppler signal and the clutter component is performed by means of the MTI (moving-target indicator) filter 114 which is constructed by digital circuits. FIG. 2 shows a response characteristic of the MTI filter 114. As illustrated in FIG. 2, the response of the MTI filter could not be steep enough to remove the clutter component sufficiently and when MTI filter is constructed to remove the clutter component sufficiently, the blood stream signal is also suppressed to an undesired extent. In this manner, the known color Doppler apparatus could not measure the blood stream of a low velocity. Further the Doppler effect appears only in the direction in which the ultrasonic beam 116 is emitted, and therefore it is theoretically impossible to detect the blood stream flowing in a direction perpendicular to the ultrasonic beam direction.

The ultrasonic beam is composed of a plurality of ultrasonic waves, which are emitted from respective vibrating elements 102 at different timings determined by delay times of the delay circuits 103. In a long range in which a distance between the vibrating element array 101 and the object is long, angles between lines normal to respective vibrating elements and lines connecting respective vibrating elements and the object are substantially same. However, in a short range in which the distance is small, these angles vary largely. The Doppler effect depends largely upon these angles, and thus when the distance is small, a large fluctuation is produced in the Doppler frequency and the measuring accuracy becomes very low. This problem could not be resolved by increasing the spatial resolution in the short range by utilizing dynamic focus.

Further, in the known color Doppler apparatus mentioned above, in addition to a usual ultrasonic pulse transmitting sequence, there is set a special sequence in which an ultrasonic pulse having a wide pulse width is transmitted for detecting a blood stream having a small velocity. Moreover, in order to increase the accuracy of the Doppler measurement, it is necessary to repeat the Doppler sequence by about ten times and an averaging process is required. Therefore, the frame rate of the color Doppler apparatus is decreased greatly as compared with the usual B-mode ultrasonic image and the spatial resolution is liable to be decreased.

SUMMARY OF THE INVENTION

The present invention has for its object to provide a novel and useful ultrasonic diagnosing apparatus, in which the blood stream having a low velocity can be easily measured without reducing the frame rate and thus decreasing the spatial frequency.

It is another object of the invention to provide an ultrasonic diagnosing apparatus in which the blood stream flowing in parallel with a direction in which the vibrating elements are aligned can be measured.

According to the invention, an ultrasonic diagnosing apparatus comprises:

a vibrating element array having a number of vibrating elements arranged side by side;

a multiplexer for selecting one of the vibrating elements;

a transmitting circuit for supplying pulses to the vibrating elements by means of the multiplexer;

a receiving circuit for amplifying an echo signal generated from a vibrating element which transmits an ultrasonic pulse and receives an ultrasonic wave reflected by an object under inspection and selected by the multiplexer;

an orthogonal detector for converting an output signal from the receiving circuit into a complex signal consisting of a real part and an imaginary part;

A/D converting means for converting said complex signal into a digital complex signal;

wave surface data storing means including plural pairs of memories, each corresponding to respective vibrating elements, each of the memory pairs storing the digital complex signal as wave surface data;

a spectrum distribution detecting means for detecting a spatial frequency from the wave surface data stored in the wave surface data storing means;

means for deriving a strength of an ultrasonic wave reflected by the object from a DC component of the spatial frequency and displaying an ultrasonic image; and means for deriving a velocity of a blood stream from a frequency component other than the DC component.

According to the invention, the electro-acoustic vibrating elements are successively connected to the transmitting circuit and receiving circuit by the multiplexer and the echo signal is converted into the complex signal representing the wave surface data with the aid of the orthogonal detector. Then, the real and imaginary parts of the complex signal, representing the wave surface data obtained from respective vibrating elements, are stored in a pair of memories and the thus stored wave surface data is sampled at suitable timings such that the ultrasonic beam is focused at a given point by the synthetic aperture method. In this manner, a series of sampled data values are derived as the spatial frequency by means of the spectrum distribution detector and the velocity of the blood stream is detected by the thus derived spatial frequency.

The spatial frequency detected by the spectrum distribution detector is related to relative positional relation between the vibrating elements and the blood cells whose positions are changed in accordance with time. For instance, when the blood cells move toward the vibrating element array, the spatial frequency has a positive frequency component, when the blood cells move away from the vibrating elements, it contains a negative frequency component, and when the blood cells move in the right or left hand direction, the spatial frequency has both positive and negative frequency components. Therefore, by analyzing the spatial frequency, it is possible to detect the blood stream which moves not only in a direction parallel to the propagating direction of the ultrasonic beam but also in the direction perpendicular to the ultrasonic wave propagating direction. The DC component of the spatial frequency represents the strength of the ultrasonic wave reflected by the stationary objects, so that by processing the DC component of the spatial frequency it is possible to display the B-mode ultrasonic image. The remaining component, i.e. the AC component of the spatial frequency, is displayed as the Doppler data representing the velocity of the blood stream.

BRIEF DESCRIPTION OF THE DRAWINGS

FIG. 2 is a schematic view illustrating the operation for separating the blood stream signal from the clutter signal in the known apparatus;

FIG. 3 is a block diagram depicting an embodiment of the ultrasonic diagnosing apparatus according to the invention;

FIG. 4 is a schematic view for explaining the principle of the synthetic aperture method;

FIGS. 5A, 5B and 5C are schematic views for explaining the principal operation for detecting a moving object according to the invention;

FIG. 6 is a schematic view explaining the distortion of the wave surface due to the movement of the object;

FIGS. 7A, 7B and 7C are schematic views illustrating the conception for changing the directivity of the ultrasonic beam;

FIG. 8 is a schematic view explaining the operation for separating the blood stream signal from the clutter signal;

FIG. 9 is a block diagram showing another embodiment of the ultrasonic diagnosing apparatus according to the invention;

FIGS. 10A, 10B and 10C are schematic views explaining the wave composition by the synthetic aperture method; and FIG. 11 is a perspective view showing the relation between the vibrating element array and spatial points.

DESCRIPTION OF THE PREFERRED EMBODIMENTS

Figure 1:
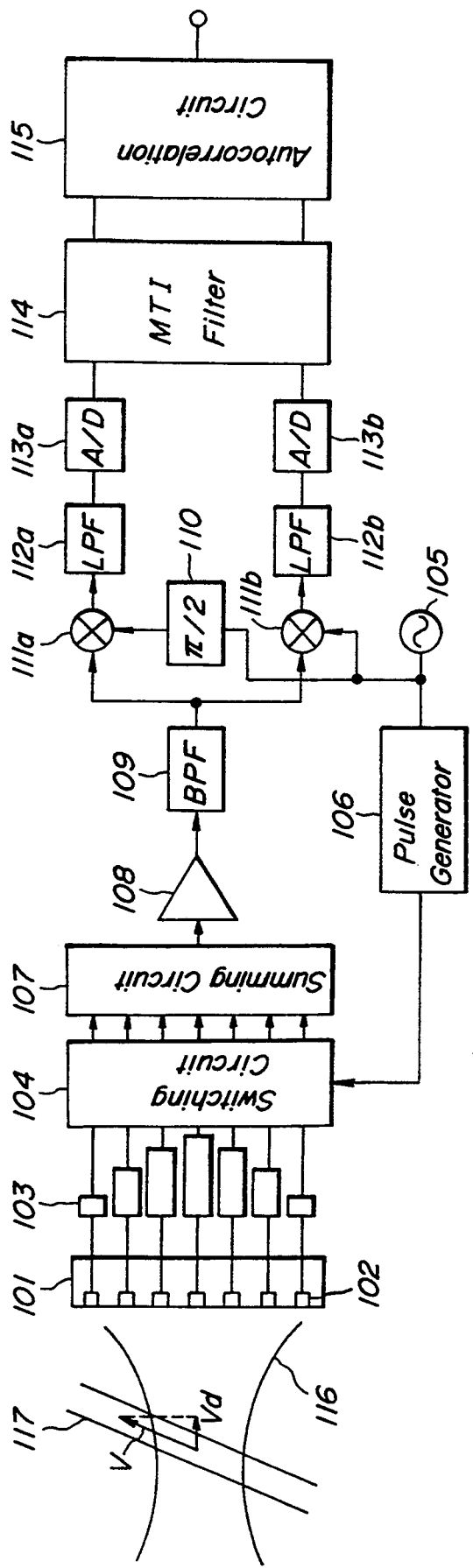
FIG. 1 is a block diagram showing a known ultrasonic diagnosing apparatus.

FIG. 3 is a block diagram showing an embodiment of the ultrasonic diagnosing apparatus according to the invention. In FIG. 3, a reference numeral 1 denotes a vibrating element array, 2-1 to 2-7 denote electro-acoustic vibrating elements, 3 denotes a wave surface of an ultrasonic pulse, 4 denotes a multiplexer, 5 denotes a signal generator, 6 denotes a pulse generator, 7 denotes a transmitting amplifier, 8 denotes a receiving amplifier, 9 denotes a STC (sensitivity time control) circuit for controlling an amplification of the receiving amplifier 8, 10 denotes a band pass filter, 11 denotes a 90-degree phase shifter, 12a, 12b denote multipliers, 13a, 13b denote low pass filters, 14a, 14b denote A/D converters, 15a, 15b denote multiplexers, 16 denotes a switching control circuit for controlling the multiplexers 4, 15a and 15b, 17 wave surface memory unit, 18 denotes a address control circuit, 19 denotes a fast Fourier transformer (FTT), and 20 represents a velocity calculating circuit. The vibrating element array 1 and multiplexer 4 are provided in a distal end of an insertion section, which is inserted into a cavity of a living body. The remaining circuits are provided in a device arranged outside the living body. Further, the wave surface memory unit 17 includes plural pairs of memories A1, B1; A2, B2, - - - A7, B7, these pairs corresponding to respective vibrating elements 2-1, 2-1,- - - 2-7.

At first, under the control of the switching control circuit 16, a first vibrating element 2-1 is selected by the multiplexer 4 and a corresponding pair of memories A1 and B1 are selected by the multiplexers 15a and 15b, respectively. Then the signal generator 5 produces a reference signal which is supplied to the pulse generator 6 to produce a pulse signal. The pulse signal is then supplied, via the transmitting amplifier 7 and multiplexer 4, to the selected vibrating element 2-1 and an ultrasonic pulse 3 is generated by this vibrating element. The ultrasonic pulse 3 is reflected by blood cells in a blood stream flowing through a blood vessel and other living tissues and the reflected ultrasonic wave is received by the vibrating element 2-1 and is converted into an echo signal. The echo signal generated the vibrating element 2-1, is supplied via the multiplexer 4, to the receiving amplifier 8 and is amplified thereby. The amplitude of the echo signal is gradually reduced in accordance with time, because the damping or decay of the ultrasonic wave is gradually increased in accordance with an increase in a distance from the vibrating element to an object by which the ultrasonic wave is reflected. Therefore, the amplification of the receiving amplifier 8 is gradually increased by means of the STC circuit 9 which is synchronously operated with the pulse signal generated by the pulse generator 6.

An output signal from the receiving amplifier 8 is passed through the BPF 10 and undesired noise is removed thereby. Then, an output signal from the BPF 10 is supplied to an orthogonal detector comprising the multipliers 12a, 12b, LPFs 13a, 13b and 90-degree phase shifter 11. Then the echo signal is converted into a complex signal g(t,x) of a base band as shown by the following equation (1).

$$g(t,x) = a(t,x) + jb(t,x) \tag{1}$$

wherein a(t,x) and b(t,x) represent real and imaginary parts of the complex signal, and x denotes a position of a vibrating element.

The real and imaginary parts of the complex signal are then supplied to A/D converters 14a and 14b, respectively and are converted thereby into digital signals. The thus derived digital real and imaginary part signals are supplied, via the multiplexers 15a and 15b, to the memory unit 17 and are stored in the first pair of memories A1 and B1, respectively. That is to say, the digital signal representing the real part (a(t,x)) of the complex signal is stored in the memory A1 and the digital signal representing the imaginary part b(t, x) of the complex signal is stored in the memory B1 as the wave surface data.

Then, the multiplexers 4, 15a and 15b are operated to connect the second vibrating element 2-2 and a second pair of memories A2 and B2 is selected, and the ultrasonic pulse is generated by the vibrating element 2-2 and an ultrasonic wave reflected by the objects is received by the vibrating element 2-2 and is converted into an echo signal. This echo signal is processed in the same manner as explained above and the digitalized real and imaginary parts of the complex signal are stored in the second pair of memories A2 and B2, respectively as wave surface data.

The above explained operation is repeated until the wave surface data obtained by using the vibrating elements 2-1 to 2-7 has been stored in the memories A1 to A7 and B1 to B7 of the memory unit 17. Next, the thus stored wave surface data is processed in accordance with the synthetic aperture method to compose or reconstruct ultrasonic images in respective wave surfaces.

FIG. 4 is a schematic view showing the synthetic aperture method. Reference numerals 21a and 21b represent objects or substances which reflect the ultrasonic wave, 22 denotes a wave surface memory and 23 denotes a composed wave surface. When the ultrasonic pulse is emitted by the vibrating element 2-1 in the vibrating element array 1 and is reflected by the substances 21a and 21b in the space, a wave surface signal 24-1 is stored in a wave surface memory 22. Similarly, in the wave surface memory 22, there are successively stored wave surface signals 24-2 to 24-7. It should be noted that positional relations in the space between respective vibrating elements 2-1 to 2-7 and the substances 21a and 21b are different from one another, so that the shape of wave surface signals 24-1 to 24-7 are different from one another. Therefore, by combining these wave surface signals 24-1 to 24-7 with each other after suitably delaying or advancing the signals such that the ultrasonic pulses generated by the vibrating elements 2-1 to 2-7 are focused at any desired point in the space, it is possible to provide the directivity for the ultrasonic pulse like as the known beam composition method using the delay circuits. This method is called the Delay and Sum method. Therefore, by processing the wave surface signals for all points in the space, it is possible to detect the distribution of the substances in the space.

It should be noted that each of the vibrating elements 2-1 to 2-7 has a broad directivity and a low directivity resolution, but by utilizing the wave surface composition method, the effective directivity of the vibrating element can be sharpened and the directivity resolution can be extremely improved. In other words, a very sharp directivity obtained by using a vibrating element having a large aperture can be obtained by moving a vibrating element having a small aperture in the space to detect the wave surface signals and by composing these wave surface signals. Therefore, this method is called the synthetic aperture method.

Next a principle for detecting a moving object will be explained with reference to FIGS. 5A, 5B and 5C. FIG. 5A shows a situation in which a stationary object exists in the space, and a set of time sequential data is stored in the wave surface memory 22 by repeating the above explained transmitting and receiving operations. The time sequential data is sampled at sampling points indicated by dots 25, and spatial data is obtained at a certain time instance as indicated by a solid line 26. Next, the time sequential data is sampled at sampling points which are delayed by 90 degrees with respect to the first sampling points 25 to derive data represented by a dotted line 27. These data denoted by the solid line 26 and dotted line 27 may be expressed by a complex signal. A variation in frequency of the spatial data is called a spatial frequency. In the condition illustrated in FIG. 5A, the spatial frequency mainly consists of a DC component. When the spatial frequency data is processed by the FFT 19 to derive a spatial frequency component, a spatial spectrum P(f) is obtained shown in FIG. 5A. This spatial spectrum indicates data at one point in the space.

FIG. 5B represents a case in which an object 21 is moving toward the vibrating element array 1. While the vibrating elements 2-1 to 2-7 are successively scanned, a distance between the object 21 and the vibrating array 1 becomes shorter and thus the wave surface data stored in the wave surface memory 22 is deviated from that shown in FIG. 5A. When the wave surface data is sampled at the same sampling timings 25, there is detected a signal component having a periodic component. When this signal component is Fourier transformed by the FFT 19, there is derived a spatial spectrum having a peak in a positive frequency range.

FIG. 6 is a schematic view explaining the phenomenon in which the wave surface data is deviated in accordance with the movement of the object 21. When the object 21 moves toward the vibrating element 2, a distance between the object and the vibrating element becomes shorter, so that time instances at which the ultrasonic wave reflected by the object 21 arrives at the vibrating element 2 becomes gradually earlier. Therefore, when the signal is sampled at the same timing, the movement of the object results in the change in phase of the sampled signal. According to the invention, the signal is sampled at two points which are separated by 90 degrees from each other to derive the complex signal, and the phase of the complex signal is changed by the movement of the object 21.

FIG. 5C is a schematic view depicting a case in which the object 21 moves in a direction along the vibrating element array 1, i.e. in a direction perpendicular to the propagating direction of the ultrasonic pulse. In such a case, for the vibrating elements 2-1 to 2-3, a spatial distance is gradually decreased, but for the vibrating elements 2-4 to 2-7, a spatial distance is gradually increased. Therefore, there is obtained a signal having positive and negative frequency components when the signal is sampled at the same timings as in the case of FIGS. 5A and 5B. These positive and negative frequency components can be distinguished from each other in the complex signal, and thus when the signal is processed by the FFT 19, there are detected a spectrum distribution having the positive and negative components.

When the object 21 moves away from the vibrating element array 1, the situation is reversed to the case shown in FIG. 5B and the negative frequency component may be obtained as the result of the Fourier transform. Furthermore, when the object moves along the vibrating element array 1 in a direction opposite to that illustrated in FIG. 5C, there is obtained the phase spectrum which is reversed to that shown in FIG. 5C, so that the direction of the movement can be detected.

In the above explanation, for the sake of simplicity, in order to detect the complex signal constituting the reflection signal at a certain focal point, the wave surface signal is sampled at two sampling points which are separated from each other by 90 degrees. However, in order to derive the complex signal, it is common to use an orthogonal detector comprising the multipliers 12a, 12b, LPFs 13a, 13b and 90-degree phase shifter 11 as illustrated in FIG. 3.

FIGS. 7A, 7B and 7C are schematic views showing the principle of changing the directivity of the ultrasonic beam. In FIG. 7A, an ultrasonic beam 30a is projected in a direction perpendicular to the plane along which the vibrating elements 2-1 to 2-7 are arranged, and FIGS. 7B and 7C show cases in which ultrasonic beams 30b and 30c are directed to right hand side and left hand side, respectively. In these figures, reference numerals 28a, 28b and 28c denote equi-phase planes, and 29a, 29b and 29c represent memories for storing sampled data in accordance with the distance. In the drawings, there are provided plural memories, the number of which is equal to the number of equi-phase planes. In practice, a much greater number of memories are provided. By changing the equi-phase planes in various manners, it is possible to attain any desired directivity.

In the present embodiment, the read-out address for the wave surface memory unit 17 is controlled by the address control circuit 18 to obtain a desired equi-phase plane and the thus derived wave surface data is processed to obtain the ultrasonic reflection image. That is to say, after all the wave surface data corresponding to the vibrating elements 2-1 to 2-7 has been stored in the wave surface memory unit 17, the read-out address is controlled by the address control circuit 18 such that wave surface data g(x) on a given equi-phase plane can be read-out. This wave surface data g(x) is then supplied to the FFT 19 and a spectrum distribution G(w) representing the spatial frequency is derived in accordance with the following equations.

$$G(w) = \int_{-l/2}^{l/2} g(x)e^{-j\omega x}dx \quad (2)$$

$$G(w) = A(w) + jB(w) \quad (3)$$

$$P(w) = \sqrt{A^2(w) + B^2(w)} \quad (4)$$

$$\theta(w) = \tan^{-1}\frac{B(w)}{A(w)} \quad (5)$$

wherein l is a length of the vibrating element array, P(w) a power spectrum and θ(w) denotes a phase spectrum.

As can be understood from the above explanation, the wave surface data g(x) is composed of the real part data A1 to A7 (a(x)) and the imaginary part data B1 to B7

(b(x)), so that by deriving the spectrum distribution G(w) with the aid of the FFT 19, it is possible to obtain the power spectrum P(w) and phase spectrum $\theta$(w) from the real part A(w) and imaginary part B(w) of the spectrum distribution in accordance with the above equations.

The spectrum distribution defined by the output signal of the FFT 19 includes the clutter signal component reflected by the stationary objects and the component reflected by the blood steam as indicated in FIG. 8. The clutter component reflected by the stationary tissues is always a DC component and thus the DC component is supplied to a digital scan converter (DSC) 61 to derive an ultrasonic image signal of B-mode, which is then supplied to a display monitor 62. The AC component of the spectrum distribution is supplied to a circuit 20 for calculating the velocity of the blood stream. At the same time, the magnitude and direction of the blood stream are derived as the Doppler signal from the shape of the frequency spectrum distribution. The magnitude of the blood stream corresponds to an average frequency of the frequency spectrum and the direction of the blood stream may be determined by the shapes of the power spectrum distribution P(w) and phase spectrum $\theta$(w) as has been explained with reference to FIG. 5. In the blood stream velocity calculating circuit 20, the frequency discrimination can be carried out easily, so that the blood stream signal, free from the clutter signal, can be easily derived without reducing the blood stream component.

The Doppler signal derived from the circuit 20 is supplied to a digital scan converter 63 to produce an image signal representing the detected blood stream and the thus derived image signal is displayed on the display monitor 62 in superimposition upon the ultrasonic image.

The present invention is not limited to the described embodiment, but many modifications and alternations may be conceived by those skilled in the art within the scope of the invention. For instance, in the above explained embodiment, there are provided seven vibrating elements 2-1 to 2-7, but the number of vibrating elements is not limited to seven and the vibrating element array may be formed by more than seven vibrating elements. For example, the array may be constructed by sixty four vibrating elements. By increasing the number of vibrating elements, the directivity of the ultrasonic beam can be increased and the spatial resolution can be further improved. Moreover, a time period for the transmitting receiving sequences for obtaining the reflection image at a certain point is made longer, and therefore it is possible to detect a blood stream having a very low velocity. Further an amount of data is increased, so that the accuracy of the Doppler measurement is increased.

In the above embodiment, the spectrum of the spatial frequency is derived by using the FFT, but it may be obtained by using any other spectrum distribution detector. The vibrating elements may be arranged along a circle or convex instead of the rectilinear arrangement. In case of using such arrangements of the vibrating elements, the equi-phase sampling may be equally performed by suitably adjusting the sampling timings with the aid of the address control circuit 18.

FIG. 9 is a block diagram showing another embodiment of the ultrasonic diagnosing apparatus according to the invention. In the present embodiment, a vibrating element array 1 is formed by a number of vibrating elements 2-1 to 2-N which are arranged side by side along a circle. The vibrating element array 1 is provided in a distal end of an insertion section of endoscope together with the multiplexer 4. The vibrating elements 2-1 to 2-N are successively selected by the multiplexer 4 and a selected vibrating element is connected to a transmitting circuit 42 and a receiving amplifier 8 by means of a signal conductor 41 which extends within a probe to be inserted into a cavity of a living body. In this manner, transmission and reception of the ultrasonic beam can be performed in a time division manner. An amplification of the receiving amplifier 8 is adjusted by a STC circuit 9 such that the amplification is gradually increased from the ultrasonic beam transmission timing. An output signal of the receiving amplifier 8 is supplied to a multiplexer 15 via band pass filter 10 and A/D converter 14. The multiplexer 15 is controlled by a switching control circuit 16 in synchronism with the multiplexer 4, so that echo signals obtained by successive vibrating elements are stored in corresponding wave surface memories 17-1 to 17-N in a wave surface memory unit 17. The writing and reading operation for these wave surface memories 17-1 to 17-N are controlled by reading address circuit 43 and writing address circuit 44. The read-out wave surface data is supplied, via summing circuit 45 and logarithm converting circuit 46, to a digital scan converter (DSC) 47 and an ultrasonic image of B-mode is displayed on a display monitor 48. The STC circuit 9 is controlled in synchronism with the write address circuit 43 and the summing operation in the summing circuit 45 and the writing operation in the DSC 47 are synchronized with the reading-out operation for the wave surface memory 17.

Now the operation of the present embodiment will be explained. At first, the multiplexers 4 and 15 are controlled by the switching control circuit 16 such that a first vibrating element 2-1 and first memory 17-1 are selected. Then, an impulse is generated by the transmitting circuit 42 and is supplied to the vibrating element 2-1 via the signal conductor 41 and multiplexer 4. An ultrasonic pulse is emitted from the vibrating element 2-1 toward living tissues and a reflected ultrasonic wave is received by the vibrating element 2-1. The vibrating element 2-1 converts the received ultrasonic wave into an electric echo signal or reflection signal, and the echo signal is supplied via the signal conductor 41 to the receiving amplifier 8 and is amplified thereby to a suitable signal level. The amplified echo signal is then supplied to the A/D converter 14 by means of the BPF 10 and is converted into a digital echo signal. Then, the digital echo signal is supplied via the multiplexer 15 to the memory 17-1 and is stored therein as the wave surface data in a time sequential manner.

Next, the multiplexers 4 and 15 are switched by the switching control circuit 16 such that the second vibrating element 2-2 and the second memory 17-2 are selectively connected into the circuit, and the transmission and reception of the ultrasonic pulse are carried out in the manner explained above. In this manner, a second digital echo signal is stored in the second memory 17-2. This operation is repeated until all the digital echo signals are stored in the memories 17-1 to 17-N.

Then, the wave surface data are summed in the summing circuit 45 by the above explained Delay and Sum method to reconstruct an ultrasonic image representing the distribution of the reflection strength of ultrasonic reflecting objects in the space. To this end the reading-out timings are controlled by the reading address circuit 44 such that an equi-phase wave surface data is read out of the memories 17-1 to 17-N.

FIGS. 10A, 10B and 10C are schematic views showing the reading address for performing the synthetic aperture method. FIG. 10A illustrates a situation in which reflection signals from 60 degrees are composed, FIG. 10B shows a situation in which reflection waves from 120 degrees are composed, and FIG. 10C shows a case in which reflection signals from 300 degrees are composed. In these figures, the wave surface memories 17-1, 17-2 - - - 17-N correspond to the vibrating elements 2-1, 2-2 - - - 2-N, respectively and the directions viewed from left to right correspond to distances. In the situation shown in FIG. 10A, the equi-phase wave surface data are summed to effect the wave surface composition. The equi-phase wave surface is determined by a geometric positional relation between respective vibrating elements 2-i and a spatial point such as points 50a and 50b illustrated in FIG. 11. That is to say, time periods during which the ultrasonic wave propagates from the vibrating elements 2-i to the spatial point differ from each other, and the reading address for the memory unit 17 is adjusted such that the differences in the propagating time periods are compensated for.

In case of detecting the reflection signal from 60 degrees, echo signals which are generated by vibrating elements which are hidden by other vibrating elements could not be utilized, so that only echo signals which are generated by a fourth of the vibrating elements 2-1 to 2-N are used. In other words, the reflection signals from 60 degrees are composed by using about one fourth of the memories 17-1 to 17-N. Similarly, in case of composing the reflection signals from 120 degrees, a area of usable memories is shifted as shown in FIG. 10B. In the situation for composing the reflection signals from 300 degrees, wave surface data read out of memories within an area illustrated in FIG. 10C are utilized.

The equi-phase wave surface for summing the wave surface data has a larger radius for a closer point and has a smaller radius for a remote point, so that the equi-phase wave surface resembles a kind of hyperbola. In this wave surface composition, the ultrasonic beam can be focussed at any desired point in the space, and therefore it is possible to attain a kind of the dynamic focus like the known beam composition using the delay lines and the decrease in the directivity resolution for closer and remote objects can be minimized.

The equi-phase wave surface data read out of the memory unit 17 are summed in the summing circuit 45 to derive the strength signal of the reflection signal at a certain point in the space, and then the reflection strength signal is detected and compressed by the logarithm converting circuit 46 and the output of this circuit is supplied to the DSC 47 in which the coordinate system of the strength signal is converted into that applied to the display 48. If necessary, in the DSC 47 there may be performed the image interpolation. Then, the image signal generated by the DSC 47 is supplied to the display 48 and is displayed thereon.

In the above explained embodiment, the vibrating elements are aligned along a circle, but they may be arranged in a convex form or rectilinear form. Even in such a case, the reflecting property of the object can be detected by performing the wave surface composition such that the summing operation is carried out to attain a desired equi-phase wave surface.

As explained above in detail, according to the invention, respective vibrating elements are selected in the time division manner to effect the transmission and reception of the ultrasonic pulse and the wave surface data is stored in the memory unit. Then, the contents of the memory unit are read out at suitable timings to effect the wave surface composition to obtain the distribution data of the reflection strength of objects in the space. Therefore, in principle, it is sufficient to provide a single signal conductor between the vibrating elements and the transmission and reception circuits. Therefore, the signal conductor can be easily installed within the ultrasonic probe having a very small diameter. Moreover, the number of the vibrating elements can be easily increased without increasing the number of the signal conductor and thus the resolution of the ultrasonic image can be improved. Further, when the vibrating elements are arranged along the circle, the ultrasonic beam can be electrically rotated at a constant speed, and thus it is possible to display a stable ultrasonic image.

Moreover, the wave surface data is stored in the memory unit and the spectrum distribution of the spatial frequency is derived by processing the wave surface data, and the reflection strength of the living tissues can be derived from the DC component of the spatial frequency and the blood stream velocity can be derived from the AC component. In this case, the reflection signal from the stationary tissues and the blood stream signal can be easily separated from each other by effecting frequency discrimination using the result of the Fourier transformation, and therefore the decay of the low frequency component can be avoided and a blood stream having a very low velocity can be detected. Furthermore, the blood stream velocity not only in the direction in which the ultrasonic beam propagates, but also in the direction perpendicular thereto can be detected from the shape of the spectrum distribution of the spatial frequency.

In the known beam composition method, the echo signals generated by all the vibrating elements are simultaneously processed to derive the blood stream information, and therefore the measurement accuracy is materially decreased for closer objects. In the present invention, the spatial frequency is determined by the mutual relation between respective blood cells and respective vibrating elements, so that the movement of the blood cells is strictly reflected upon the spatial frequency even for a short range and the blood stream velocity can be measured accurately.

Further in the present invention, the ultrasonic image data is derived from the DC component of the output of the spectrum distribution detector and the blood steam velocity is derived from the AC component, so that it is no longer necessary to provide a special transmission sequence for measuring the blood stream velocity. In the known method, it is necessary to repeat the transmission sequence by about ten times and an average of velocities is derived. However, in the present invention, such an averaging operation is not necessary at all, and the frame rate can be equal to that of the B-mode image. Moreover, the distribution of the blood stream velocity can be visualized at a high response speed in the color Doppler mode. Further, the blood stream velocity is measured by a number of transmission sequences, and therefore the minimum measuring period can be reduced and thus a blood stream having a very small velocity within a very thin blood vessel can be detected. Since the blood stream velocity in the direction parallel with the vibrating array can be measured and thus stomach organs can be diagnosed accurately.

What is claimed is:

1. An ultrasonic diagnosing apparatus comprising: a transmitting circuit for outputting pulses;
   a vibrating element array having a number of vibrating elements arranged side by side;
   a multiplexer for receiving said pulses from said transmitting circuit and selectively providing said pulses to one of said vibrating elements such that said one of said vibrating elements (i) transmits an ultrasonic pulse in response to said pulses and (ii) receives an ultrasonic wave reflected by an object under inspection and generates an echo signal based on said reflected ultrasonic wave;
   a receiving circuit for amplifying said echo signal generated from said one of said vibrating elements to provide an amplified echo signal;
   an orthogonal detector for converting said amplified echo signal from the receiving circuit into a complex signal consisting of a real part and an imaginary part;
   A/D converting means for converting said complex signal into a digital complex signal;
   wave surface data storing means including plural pairs of memories said memory pairs corresponding to respective vibrating elements and storing a said digital complex signal, provided by its respective vibrating element, as wave surface data;
   spectrum distribution detecting means for detecting a spatial frequency from the wave surface data stored in said wave surface data storing means;
   means for deriving an ultrasonic wave reflection strength from a DC component of the spatial frequency detected by said spectrum distribution detecting means and displaying an ultrasonic image based on said ultrasonic wave reflection strength; and
   means for deriving a velocity of a blood stream from frequency components, of said spatial frequency detected by said spectrum distribution detecting means, other than said DC component.

2. An ultrasonic diagnosing apparatus according to claim 1, wherein said means for deriving the ultrasonic wave reflection strength from the DC component of the spatial frequency and displaying the ultrasonic image comprises a digital scan converter for generating a B-mode ultrasonic image signal and a display monitor for receiving the B-mode ultrasonic image signal and displaying the ultrasonic image; and said means for deriving the velocity of the blood stream from the frequency component other than the DC component comprises a circuit for converting the velocity of the blood stream into an image signal of the blood stream and means for displaying the blood stream image signal in superimposition on the ultrasonic image displayed on the display monitor.

3. An ultrasonic diagnosing apparatus according to claim 1, wherein said transmitting circuit comprises a signal generator for generating a reference signal and a pulse generator for generating a pulse signal synchronized with the reference signal; and said orthogonal detector for converting the output signal from the receiving circuit into the complex signal comprises first and second multipliers for multiplying the output signal from the receiving circuit with said reference signal and a signal which is obtained by phase-shifting said reference signal by 90 degrees to derive the real and imaginary parts of the complex signal, and first and second low pass filters for cutting off high frequency components of output signals of said first and second multipliers, respectively.

4. An ultrasonic diagnosing apparatus according to claim 1, wherein said spectrum distribution detecting means comprises a fast Fourier transformer.

5. An ultrasonic diagnosing apparatus according to claim 1, wherein said receiving circuit comprises:
   an amplifier having a variable amplification, and
   a control circuit for increasing the amplification of said amplifier, in synchronism with outputting of said pulse signals by said pulse generator, in accordance with an elapsing time.

6. An ultrasonic diagnosing apparatus according to claim 1, wherein said vibrating element array is provided in a distal end of an insertion section of said apparatus insertable into a cavity of a living body.

* * * * *